United States Patent [19]
Borgerding et al.

[11] Patent Number: 6,058,327
[45] Date of Patent: May 2, 2000

[54] IMPLANTABLE DEVICE WITH AUTOMATIC SENSING ADJUSTMENT

[75] Inventors: Girard B. Borgerding, Minneapolis; David K. L. Peterson, Circle Pines; Gerald P. Borgerding, Long Lake, all of Minn.

[73] Assignee: Medtronic, Inc., Minneapolis, Minn.

[21] Appl. No.: 09/112,917

[22] Filed: Jul. 9, 1998

[51] Int. Cl.[7] .............. A61N 1/362; A61N 1/365
[52] U.S. Cl. ........................................................ 607/9
[58] Field of Search .................................... 607/9, 17

[56] References Cited

U.S. PATENT DOCUMENTS

| | | | |
|---|---|---|---|
| 4,312,355 | 1/1982 | Funke | 607/9 |
| 4,316,472 | 2/1982 | Mirowski et al. | 607/9 |
| 4,375,817 | 3/1983 | Engle et al. | 607/4 |
| 4,379,459 | 4/1983 | Stein | 607/9 |
| 4,384,585 | 5/1983 | Zipes | 607/9 |
| 4,577,633 | 3/1986 | Berkovits et al. | 607/15 |
| 4,587,970 | 5/1986 | Holley et al. | 607/15 |
| 4,726,380 | 2/1988 | Vollmann et al. | 607/15 |
| 4,727,877 | 3/1988 | Kallok | 607/5 |
| 4,800,883 | 1/1989 | Winstrom | 607/7 |
| 4,830,006 | 5/1989 | Haluska et al. | 607/4 |
| 4,880,005 | 11/1989 | Pless et al. | 607/15 |
| 4,928,688 | 5/1990 | Mower | 607/9 |
| 4,949,719 | 8/1990 | Pless et al. | 607/7 |
| 4,953,551 | 9/1990 | Mehra et al. | 607/5 |
| 5,117,824 | 6/1992 | Keimel et al. | 607/5 |
| 5,163,427 | 11/1992 | Keimel | 607/5 |
| 5,188,105 | 2/1993 | Keimel | 607/5 |
| 5,269,298 | 12/1993 | Adams et al. | 607/5 |
| 5,269,300 | 12/1993 | Kelly et al. | 607/4 |
| 5,403,356 | 4/1995 | Hill et al. | 607/14 |
| 5,540,727 | 7/1996 | Tockman et al. | 607/18 |
| 5,620,466 | 4/1997 | Haefner et al. | 607/5 |
| 5,720,768 | 2/1998 | Verboven-Nelissen | 607/9 |
| 5,755,738 | 5/1998 | Kim et al. | 607/9 |
| 5,772,691 | 6/1998 | Routh et al. | 607/9 |
| B1 4,830,006 | 10/1997 | Haluska et al. | 607/4 |
| B1 4,880,005 | 10/1996 | Pless et al. | 607/15 |

FOREIGN PATENT DOCUMENTS 9218198   10/1992   WIPO ..................... A61N 1/39

OTHER PUBLICATIONS

"Onset and Stability for Ventricular Tachyarrhythmia Detection in an Implantable Pacer–Cardioverter–Defibrillator" by Olson et al., published in *Computers in Cardiology*, Oct. 7–10, 1986, IEEE Computer Society Press, pp. 167–170.

"Automatic Tachycardia Recognition", by Arzbaecher et al., published in PACE, May–Jun., 1984, pp. 541–547.

*Primary Examiner*—Carl H. Layno
*Attorney, Agent, or Firm*—Reed A. Duthler; Harold R. Patton

[57] ABSTRACT

An implantable cardiac pacemaker and a method of its operation. The pacemaker delivers pacing pulses to a first chamber of a patient's heart and senses depolarizations of a second chamber of the patient's heart. The amplifier for sensing depolarizations of the second chamber of the patient's heart defines a base sensing threshold and, responsive to delivery of a pacing pulse to the first chamber of the patient's heart for defines an increased sensing threshold greater than the base sensing threshold. The increased sensing threshold persists for a defined period of time following delivery of a pacing pulse to the first chamber of the patient's heart and thereafter gradually decreases from the increased sensing threshold to the base sensing threshold.

10 Claims, 5 Drawing Sheets

IMPLANTABLE DEVICE WITH AUTOMATIC SENSING ADJUSTMENT

BACKGROUND OF THE INVENTION

The present invention relates to medical stimulators and leads generally, and more particularly to implantable pacemakers, cardioverters and defibrillators.

In the context of implantable pacemakers or other stimulators which stimulate and sense electrical activity in multiple chambers of the heart, it has been conventional to provide a blanking period for the amplifier associated with one chamber of the heart, during delivery of a pacing pulse to another chamber of the heart. An earlier example of this feature may be found in U.S. Pat. No. 4,312,355 issued to Funke. It is also conventional to provide a blanking period for the sense amplifier coupled to the chamber being paced, during delivery of the pacing pulse.

Particularly in the context of devices which detect tachyarrhythmias, amplifiers have been developed which automatically adjust the effective sensing threshold, in order to facilitate sensing of the relatively lower amplitude depolarization wave forms that may be associated with tachyarrhythmias without sensing the repolarization wave forms associated with depolarizations occurring during normal sinus rhythm. The adjusting of the effective sensing threshold may be accomplished by adjusting the gain of the amplifier and comparing the amplified signal to a fixed threshold and/or by adjusting the threshold level of the detector associated with the amplifier, which adjustments should be understood to be equivalent alternatives in the context of the present invention. One such auto adjusting amplifier is disclosed in U.S. Pat. No. 5,117,824 issued to Keimel et al, incorporated herein by reference in its entirety. An alternative implementation of an auto adjust amplifier is disclosed in U.S. Pat. No. 5,269,300 issued to Kelly et al., also incorporated herein by reference in its entirety. In these references, following a detected depolarization, the amplifier is automatically adjusted so that the effective sensing threshold is set to be equal to a predetermined portion of the amplitude of the sensed depolarization, and the effective sensing threshold decays thereafter to a lower or base sensing threshold. Following delivery of a pacing pulse, in the system disclosed in the Kiemel et al patent, no adjustment is made to the sensing threshold, while in the Kelly et al. patent, following delivery of a pacing pulse the effective sensing threshold is set to a preset value and remains at this value for a defined period of time, after which the threshold decays to the lower or base value.

Simply employing such auto adjusting amplifiers in the context of a device which paces and senses in multiple chambers of the heart does provide a useful and workable device. However, this approach does not address the difficulties which arise when a depolarization in one chamber of the heart occurs during a blanking period initiated in response to delivery of a pacing pulse to the opposite chamber of the heart. In this circumstance, the depolarization signal may go unsensed, in turn interfering with detection of an ongoing tachyarrhythmia.

SUMMARY OF THE INVENTION

The present invention addresses this problem of sensing in one chamber following pacing in another chamber by automatically adjusting the effective sensing threshold in the chamber not being paced to a predefined amplitude selected to be large enough to prevent sensing of the pacing pulse delivered to the chamber being paced, while still allowing sensing of depolarizations in the chamber not being paced. The effective sensing threshold is set at this defined level for a period of time following the pacing pulse delivered to the paced chamber. The blanking period of the chamber not being paced is preferably minimized to include substantially only the delivered pacing pulse and the fast recharge pulse thereafter.

In a preferred embodiment of the invention following setting of the sensing threshold at the defined level for a predetermined period, the effective sensing threshold is allowed to decay to a lower or base value. In a most preferred embodiment of the present invention, the automatic adjustment of the threshold of the sense amplifier associated with a first chamber of the heart following delivery of a pacing pulse to a second chamber of the heart is embodied in an amplifier which also adjusts its effective sensing threshold of the amplifier after sensing and/or pacing in the first chamber. In such embodiments, the decay time of the effective sensing threshold following a pacing pulse delivered to the second chamber of the heart is preferably less than the decay time of the effective sensing threshold following sensing and/or pacing in the first chamber.

In some preferred embodiments, the adjustment of the sensing threshold in a first chamber of the heart in response to delivery of the pacing pulse to a second chamber of the heart is only undertaken if the defined lower or base sensitivity threshold level associated with the amplifier is less than a preset value.

DETAILED DESCRIPTION OF THE PREFERRED EMBODIMENT

Figure 1:
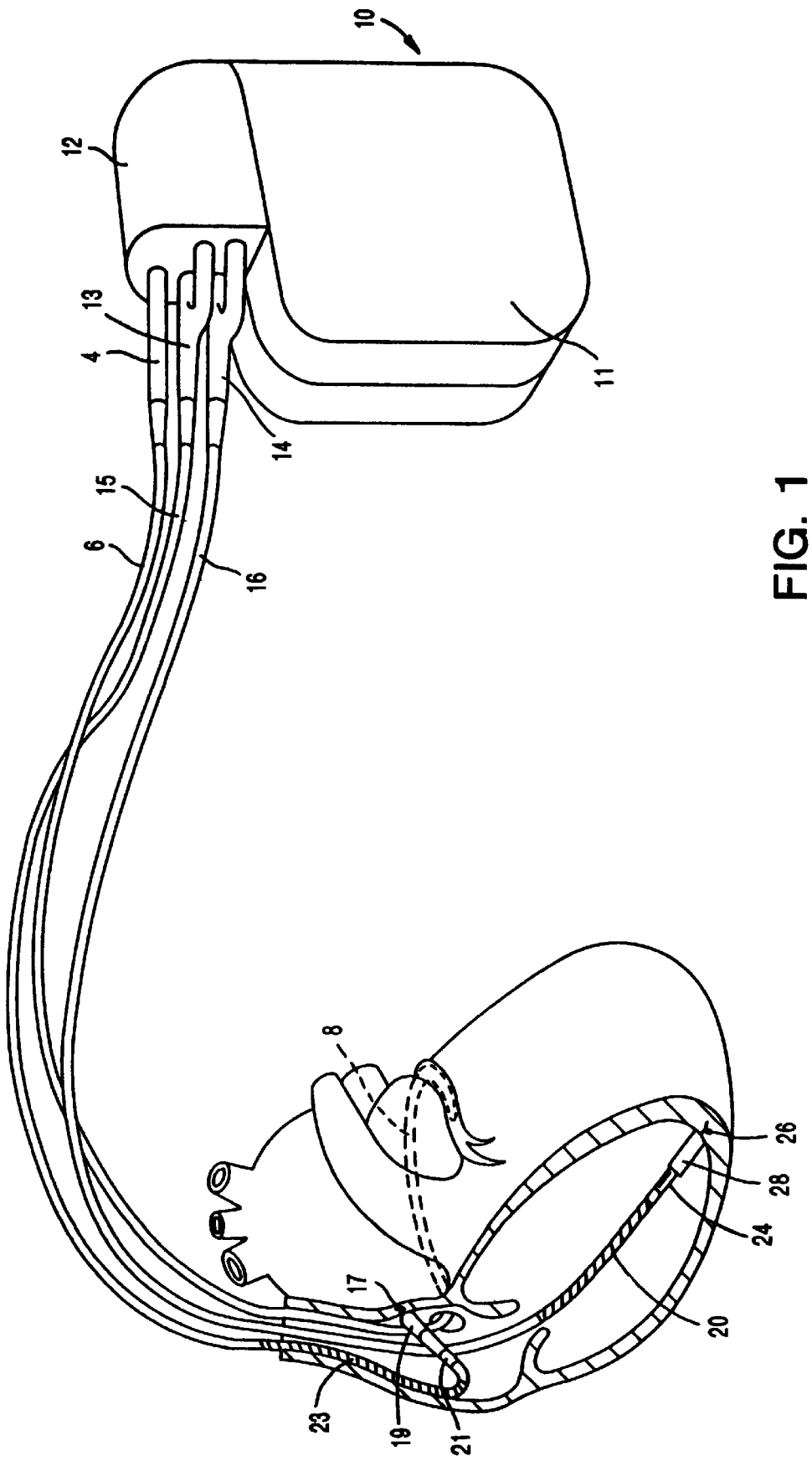
FIG. 1 illustrates a an implantable defibrillator and lead system in which the present invention may be practiced.

FIG. 1 illustrates a defibrillator and lead set according to the present invention. The ventricular lead includes an elongated insulative lead body 16, carrying three concentric coiled conductors, separated from one another by tubular insulative sheaths. Located adjacent the distal end of the lead are a ring electrode 24, an extendable helix electrode 26, mounted retractably within an insulative electrode head 28, and an elongated coil electrode 20. Each of the electrodes is coupled to one of the coiled conductors within the lead body 16. Electrodes 24 and 26 are employed for cardiac pacing and for sensing ventricular depolarizations. At the proximal end of the lead is a bifurcated connector 14 which carries three electrical connectors, each coupled to one of the coiled conductors. The defibrillation electrode 20 may be fabricated from platinum, platinum alloy or other materials known to be usable in implantable defibrillation electrodes and may be about 5 cm in length.

The atrial/SVC lead includes an elongated insulative lead body 15, carrying three concentric coiled conductors, separated from one another by tubular insulative sheaths, corresponding to the structure of the ventricular lead. Located adjacent the J-shaped distal end of the lead are a ring electrode 21 and an extendable helix electrode 17, mounted retractably within an insulative electrode head 19. Each of the electrodes is coupled to one of the coiled conductors within the lead body 15. Electrodes 17 and 21 are employed for atrial pacing and for sensing atrial depolarizations. An elongated coil electrode 23 is provided, proximal to electrode 21 and coupled to the third conductor within the lead body 15. Electrode 23 preferably is 10 cm in length or greater and is configured to extend from the SVC toward the tricuspid valve. In one preferred embodiment tested by the inventors, approximately 5 cm of the right atrium/SVC electrode was located in the right atrium, with the remaining 5 cm located in the SVC. At the proximal end of the lead is a bifurcated connector 13 which carries three electrical connectors, each coupled to one of the coiled conductors.

The coronary sinus lead includes an elongated insulative lead body 6, carrying one coiled conductor, coupled to an elongated coiled defibrillation electrode 8. Electrode 8, illustrated in broken outline, is located within the coronary sinus and great vein of the heart. At the proximal end of the lead is a connector plug 4 which carries an electrical connector, coupled to the coiled conductor. The coronary sinus/great vein electrode 8 may be about 5 cm in length.

An implantable pacemaker/cardioverter/defibrillitor 10 is shown in combination with the leads, with the lead connector assemblies 4, 13 and 14 inserted into the connector block 12. Optionally, insulation of the outward facing portion of the housing 11 of the pacemaker/cardioverter/defibrillator 10 may be provided using a plastic coating, for example parylene or silicone rubber, as is currently employed in some unipolar cardiac pacemakers. However, the outward facing portion may instead be left uninsulated, or some other division between insulated and uninsulated portions may be employed. The uninsulated portion of the housing 11 optionally serves as a subcutaneous defibrillation electrode, used to defibrillate either the atria or ventricles.

Figure 2:
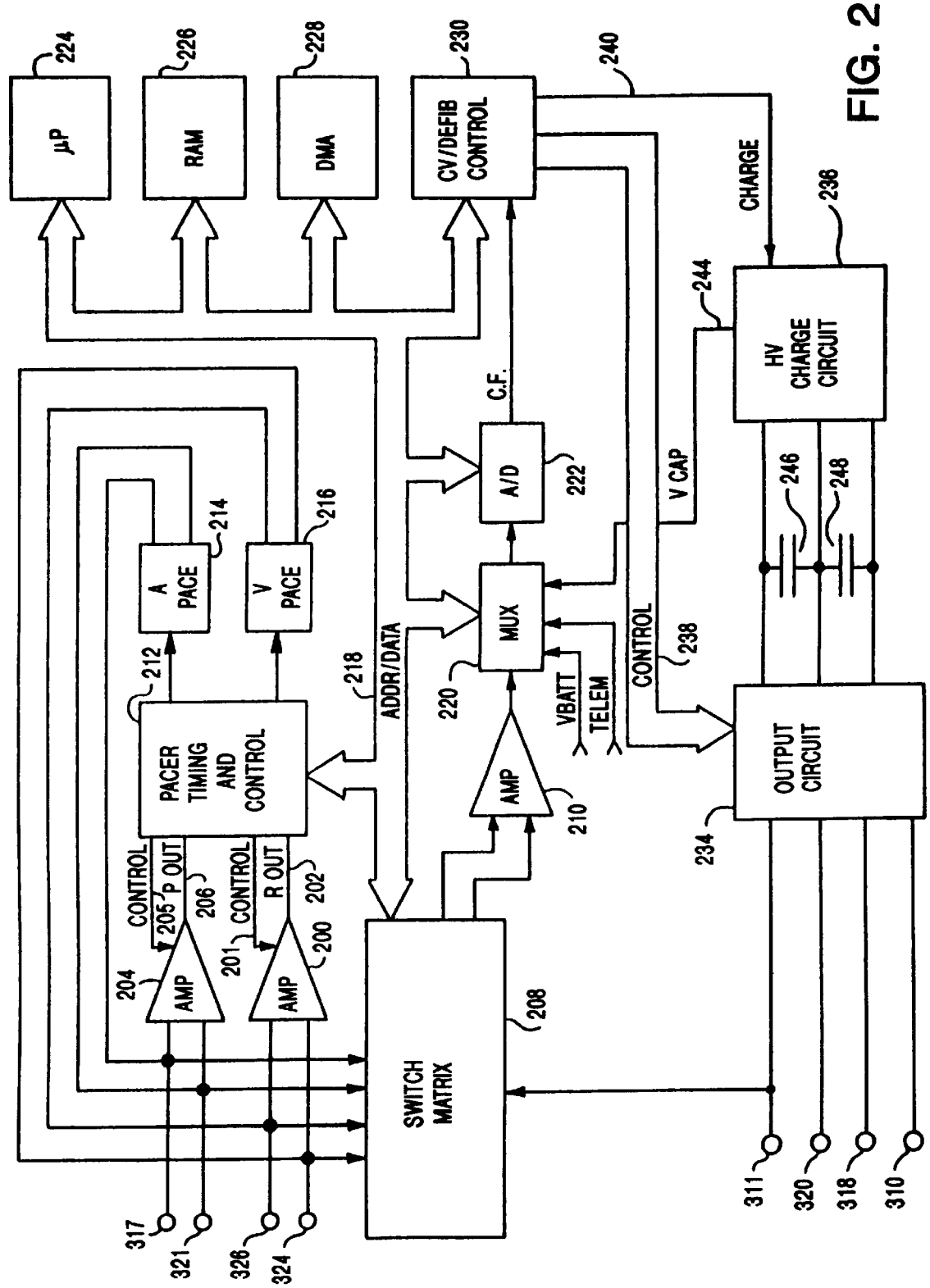
FIG. 2 illustrates a functional schematic diagram of an implantable pacemaker/cardioverter/defibrillator in which the invention may usefully be practiced.

FIG. 2 is a functional schematic diagram of an implantable pacemaker/cardioverter/defibrillator in which the present invention may usefully be practiced. This diagram should be taken as exemplary of one type of device in which the invention may be embodied, and not as limiting, as it is believed that the invention may usefully be practiced in a wide variety of device implementations, including cardiac pacemakers which do not provide high voltage cardioversion and defibrillation therapies.

The device as illustrated is provided with an electrode system including electrodes as illustrated in FIG. 1. The correspondence to the illustrated electrodes is as follows. Optional electrode 310 corresponds to electrode 11, and is the uninsulated portion of the housing of the implantable pacemaker/cardioverter/defibrillator. Electrode 320 corresponds to electrode 20 and is a defibrillation electrode located in the right ventricle. Electrode 311 corresponds to electrode 23, and is located in the right atrium and SVC. Electrode 318 corresponds to electrode 8 and is a defibrillation electrode located in the coronary sinus and great vein. Electrodes 324 and 326 correspond to electrodes 24 and 26, and are used for sensing and pacing in the ventricle. Electrodes 317 and 321 correspond to electrodes 17 and 19 and are used for pacing and sensing in the atrium.

Electrodes 310, 311, 318 and 320 are coupled to high voltage output circuit 234. High voltage output circuit 234 includes high voltage switches controlled by CV/defib control logic 230 via control bus 238. The switches within circuit 234 control which electrodes are employed and which are coupled to the positive and negative terminals of the capacitor bank including capacitors 246 and 248 during delivery of the defibrillation pulses.

Electrodes 324 and 326 are located on or in the ventricle and are coupled to the R-wave amplifier 200, which preferably takes the form of an automatically adjusted amplifier according to the present invention, providing an adjustable sensing threshold as a function of the measured R-wave amplitude and providing an increased sensing threshold following pacing pulses delivered to the atrium. Operation of Amplifier 200 is controlled by pacing circuitry 212 via control lines 201. A signal is generated on R-out line 202 whenever the signal sensed between electrodes 324 and 326 exceeds the present sensing threshold.

Electrodes 317 and 321 are located on or in the atrium and are coupled to the P-wave amplifier 204, which preferably also takes the form of an automatically adjusted amplifier according to the present invention, providing an adjustable sensing threshold as a function of the measured P-wave amplitude and providing an increased sensing threshold following pacing pulses delivered to the ventricle. Operation of Amplifier 204 is controlled by pacing circuitry 212 via control lines 205. A signal is generated on P-out line 206 whenever the signal sensed between electrodes 317 and 321 exceeds the present sensing threshold. The operation of amplifiers 204 and 206 is discussed in more detail below in conjunction with FIGS. 3, 4 and 5.

Switch matrix 208 is used to select which of the available electrodes are coupled to wide band (2.5–100 Hz) amplifier 210 for use in digital signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known in the prior art. An exemplary apparatus is disclosed of accomplishing pacing, cardioversion and defibrillation functions follows. The pacer timing/control circuitry 212 includes programmable digital counters which control the basic time intervals associated with DDD, VVI, DVI, VDD, AAI, DDI and other modes of single and dual chamber pacing well known to the art. Circuitry 212 also controls escape intervals associated with anti-tachyarrhythmia pacing in both the atrium and the ventricle, employing any anti-tachyarrhythmia pacing therapies known to the art.

Intervals defined by pacing circuitry 212 include atrial and ventricular pacing escape intervals, the refractory periods during which sensed P-waves and R-waves are ineffective to restart timing of the escape intervals and the pulse widths of the pacing pulses and all interval associated with the automatic adjustments of effective sensing thresholds discussed in more detail below. The durations of these intervals are determined by microprocessor 224, in response to stored data in memory 226 and are communicated to the pacing circuitry 212 via address/data bus 218. Pacer circuitry 212 also determines the amplitude of the cardiac pacing pulses under control of microprocessor 224.

During pacing, the escape interval counters within pacer timing/control circuitry 212 are reset upon sensing of R-waves and P-waves as indicated by a signals on lines 202 and 206, and in accordance with the selected mode of pacing on time-out trigger generation of pacing pulses by pacer output circuitry 214 and 216, which are coupled to electrodes 317, 321, 324 and 326. The escape interval counters are also reset on generation of pacing pulses, and thereby control the basic timing of cardiac pacing functions, including anti-tachyarrhythmia pacing. The durations of the intervals defined by the escape interval timers are determined by microprocessor 224, via data/address bus 218. The value of the count present in the escape interval counters when reset by sensed R-waves and P-waves may be used to measure the durations of R-R intervals, P-P intervals, P-R intervals and R-P intervals, which measurements are stored in memory 226 and used to detect the presence of tachyarrhythmias.

Microprocessor 224 operates as an interrupt driven device, under control of a stored program in its read only memory and is responsive to interrupts from pacer timing/control circuitry 212 corresponding to the occurrence sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts.

For example, in response to a sensed or paced ventricular depolarization or R-wave, the intervals separating that R-wave from the immediately preceding R-wave, paced or sensed (R-R interval) and the interval separating the paced or sensed R-wave from the preceding atrial depolarization, paced or sensed (P-R interval) may be stored. Similarly, in response to the occurrence of a sensed or paced atrial depolarization (P-wave), the intervals separating the sensed P-wave from the immediately preceding paced or sensed atrial contraction (P-P interval) and the interval separating the sensed P-wave from the immediately preceding sensed or paced ventricular depolarization (R-P interval) may be stored. Preferably, a portion of the memory 226 (FIG. 4) is configured as a plurality of recirculating buffers, capable of holding a preceding series of measured intervals, which may be analyzed in response to the occurrence of a pace or sense interrupt to determine whether the patient's heart is presently exhibiting atrial or ventricular tachyarrhythmia.

Detection of atrial or ventricular tachyarrhythmias, as employed in the present invention, may correspond to tachyarrhythmia detection algorithms known to the art. For example, presence of atrial or ventricular tachyarrhythmia may be confirmed by means of detection of a sustained series of short R-R or P-P intervals of an average rate indicative of tachyarrhythmia or an unbroken series of short R-R or P-P intervals. The suddenness of onset of the detected high rates, the stability of the high rates, or a number of other factors known to the art may also be measured at this time. Appropriate ventricular tachyarrhythmia detection methodologies measuring such factors are described in U.S. Pat. No. 4,726,380, issued to Vollmann, U.S. Pat. No. 4,880,005, issued to Pless et al. and U.S. Pat. No. 4,830,006, issued to Haluska et al., all incorporated herein by reference in their entireties. An additional set of tachycardia recognition methodologies is disclosed in the article "Onset and Stability for Ventricular Tachyarrhythmia Detection in an Implantable Pacer-Cardioverter-Defibrillator" by Olson et al., published in *Computers in Cardiology*, Oct. 7–10, 1986, IEEE Computer Society Press, pages 167–170, also incorporated herein in its entirety. However, one of the advantages of the present invention is that it is believed practicable in conjunction with most prior art tachycardia detection algorithms. Atrial fibrillation detection methodologies in particular are disclosed in Published PCT Application Ser. No. US92/02829, Publication No. WO92/18198, by Adams et al., and in the article "Automatic Tachycardia Recognition", by Arzbaecher et al., published in PACE, May–June, 1984, pp. 541–547, both of which are incorporated by reference in their entireties.

Because the accurate detection of arrhythmias using measured intervals between R-waves and P-waves is dependent on accurate sensing of the occurrences of these depolarization signals, the automatic effective sensing threshold adjustment provided by the present invention is particularly valuable in the context of ant-tachyarrhythmia devices. However, the improved sensing accuracy is also valuable in the context of anti-bradycardia pacemakers as well, particularly in the context of mode-switching features intended to prevent such pacemakers from pacing the heat at inappropriately high rates.

In the event that an atrial or ventricular tachyarrhythmia is detected, and an anti-tachyarrhythmia pacing regimen is desired, appropriate timing intervals for controlling generation of anti-tachyarrhythmia pacing therapies are loaded from microprocessor 224 into the pacer timing and control circuitry 212, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are incorporated herein by reference in their entireties may also be used.

In the event that generation of a cardioversion or defibrillation pulse is required, microprocessor 224 employs an escape interval counter to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246 and 248 via charging circuit 236, under control of high voltage charging control lines 240 and 242. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer tiring/control circuitry 212. Following delivery of the fibrillation or tachycardia therapy the microprocessor then returns the device to cardiac pacing and awaits the next successive interrupt due to pacing or the occurrence of a sensed atrial or ventricular depolarization.

One embodiment of an appropriate system for delivery and synchronization of ventricular cardioversion and defibrillation pulses and for controlling the timing functions related to them is disclosed in more detail in commonly assigned U.S. Pat. No. 5,188,105 by Keimel, issued Feb. 23, 1993, incorporated herein by reference in its entirety. Embodiments of appropriate systems for delivery and synchronization of atrial cardioversion and defibrillation pulses and for controlling the timing functions related to them are disclosed in more detail in U.S. Pat. No. 5,269,298 by Adams et al., issued Dec. 14, 1993 and in U.S. Pat. No. 4,316,472 by Mirowski et al., issued Feb. 23, 1982, both incorporated herein by reference in their entireties.

However, any known cardioversion or defibrillation pulse control circuitry is believed usable in conjunction with the present invention. For example, circuitry controlling the timing and generation of cardioversion and defibrillation pulses as disclosed in U.S. Pat. No. 4,384,585, issued to Zipes on May 24, 1983, in U.S. Pat. No. 4,949,719 issued to Pless et al., cited above, and in U.S. Pat. No. 4,375,817, issued to Engle et al., all incorporated herein by reference in their entireties may also be employed.

In the illustrated device, delivery of the cardioversion or defibrillation pulses is accomplished by output circuit 234, under control of control circuitry 230 via control bus 238. Output circuit 234 determines whether a monophasic or biphasic pulse is delivered, the polarity of the electrodes and which electrodes are involved in delivery of the pulse. Output circuit 234 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877, incorporated by reference in its entirety.

An example of circuitry which may be used to control delivery of monophasic pulses is set forth in commonly assigned U.S. Pat. No. 5,163,427, by Keimel, issued Nov. 17, 1992, also incorporated herein by reference in its entirety. However, output control circuitry as disclosed in U.S. Pat. No. 4,953,551, issued to Mehra et al. on Sep. 4, 1990 or U.S. Pat. No. 4,800,883, issued to Winstrom on Jan. 31, 1989 both incorporated herein by reference in their entireties, may also be used in conjunction with a device embodying the present invention for delivery of biphasic pulses.

In the event that, as in FIG. 1, both atrial and ventricular defibrillation are available, ventricular defibrillation may be accomplished using higher pulse energy levels than required for atrial defibrillation and may employ the same or a different electrode set. For example, electrodes 310, 311, 318 and 320 or only electrodes 311, 318 and 320 may be employed for atrial defibrillation. Electrodes 311, 320 and 310 might be employed for ventricular defibrillation, with electrode 311 (right atrium/SVC) coupled to electrode 310 (device housing). Alternatively, electrodes 310, 318 and 320 may be employed, with electrode 318 (coronary sinus/great vein) coupled to electrode 310. As a further alternative, electrodes 311, 310, 318 and 323 might all be employed for ventricular defibrillation, with electrodes 310, 311 and 323 coupled in common. As yet another alternative, only electrodes 310 and 320 might be employed for ventricular defibrillation. added or substituted for either of electrodes 311 or 318 for treating ventricular fibrillation.

One particularly desirable embodiment of the invention employs only the right atrial/SVC electrode 311, the coronary sinus/great vein electrode 318 and the right ventricular electrode 320. During atrial defibrillation, electrodes 320 and 318 are coupled in common with one another, and the atrial defibrillation pulse is delivered between these electrodes and electrode 311. During ventricular defibrillation, electrodes 311 and 318 are coupled in common with one another, and the ventricular defibrillation pulse is delivered between these electrodes and electrode 320. This particular set of electrodes thus provides optimized defibrillation pulse regimens for both atrial and ventricular defibrillation, by simply switching the connection of the coronary sinus/great vein electrode.

In modern implantable cardioverter/defibrillators, the particular therapies are programmed into the device ahead of time by the physician, and a menu of therapies is typically provided. For example, on initial detection of an atrial or ventricular tachycardia, an anti-tachycardia pacing therapy may be selected and delivered to the chamber in which the tachycardia is diagnosed or to both chambers. On redetection of tachycardia, a more aggressive anti-tachycardia pacing therapy may be scheduled. If repeated attempts at anti-tachycardia pacing therapies fail, a higher level cardioversion pulse may be selected thereafter. Therapies for tachycardia termination may also vary with the rate of the detected tachycardia, with the therapies increasing in aggressiveness as the rate of the detected tachycardia increases. For example, fewer attempts at anti-tachycardia pacing may be undertaken prior to delivery of cardioversion pulses if the rate of the detected tachycardia is above a preset threshold. The references cited above in conjunction with descriptions of prior art tachycardia detection and treatment therapies are applicable here as well.

In the event that atrial or ventricular fibrillation is identified, the typical therapy will be delivery of a high amplitude defibrillation pulse, typically in excess of 10 joules in the case of ventricular fibrillation and about 1 joule or less in the case of atrial defibrillation. Lower energy levels will be employed for cardioversion. As in the case of currently available implantable pacemakers/cardioverter/defibrillators, and as discussed in the above-cited references, it is envisioned that the amplitude of the defibrillation pulse may be incremented in response to failure of an initial pulse or pulses to terminate fibrillation. Prior art patents illustrating such pre-set therapy menus of anti-tachyarrhythmia therapies include the above-cited U.S. Pat. No. 4,830,006, issued to Haluska, et al., U.S. Pat. No. 4,726,380, issued to Vollmann et al. and U.S. Pat. No. 4,587,970, issued to Holley et al.

Figure 3:
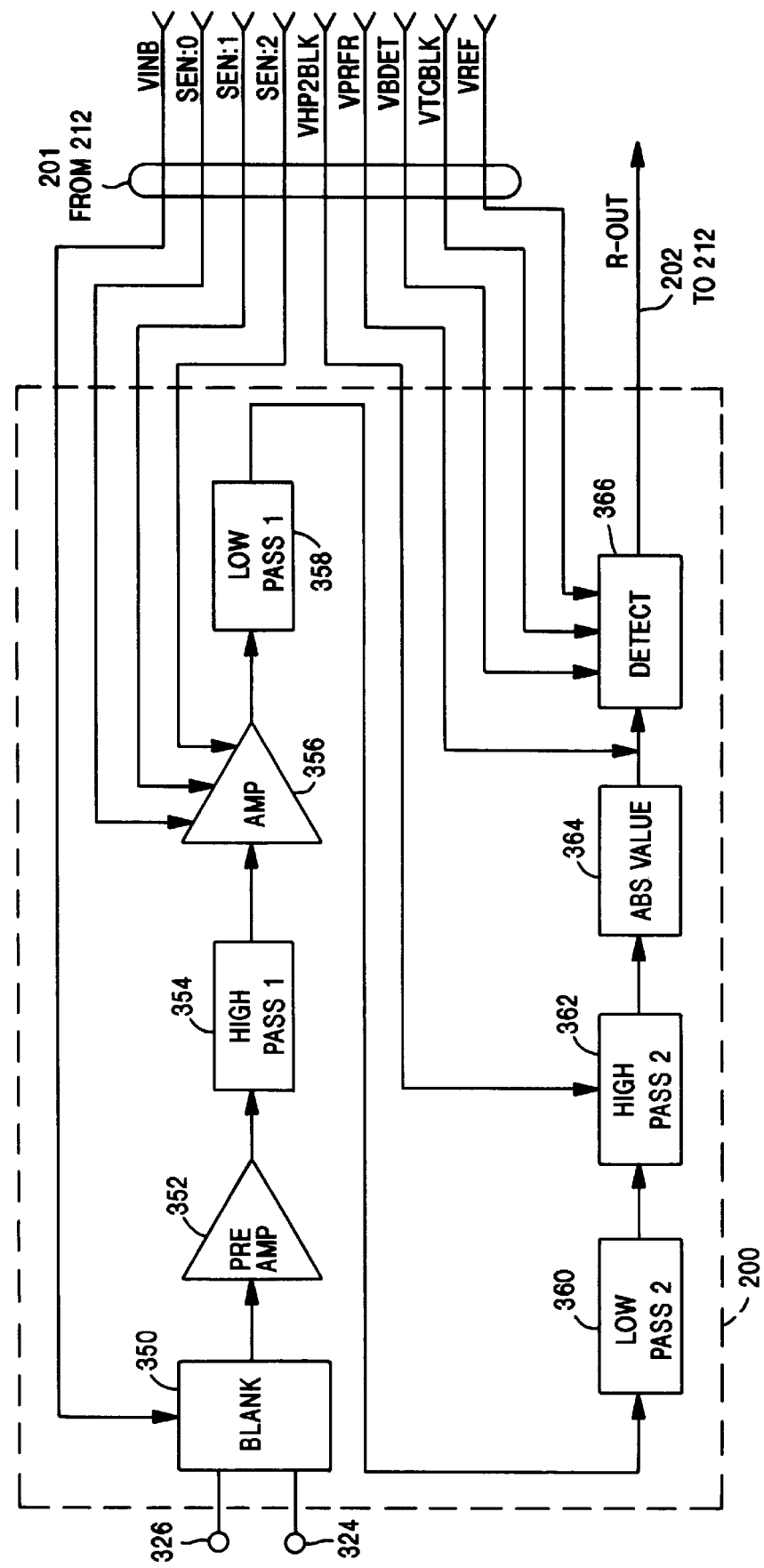
FIG. 3 illustrates a functional schematic diagram of a sense amplifier embodying the present invention.

FIG. 3 is a functional block diagram of amplifier 200 illustrated in FIG. 2. This diagram illustrates the basic functional components of the amplifier and their interconnection to the pacer timing and control circuitry 212. Signals from the ventricular electrodes 324 and 326 first pass through blanking switches 350, which operate to disconnect the amplifier from the electrodes during delivery of an atrial pacing pulse, during the duration of a ventricular input blanking signal on line VINB, which extends through the delivered atrial pacing pulse and during the fast recharge period thereafter. Depolarization signals passing through blanking switches 350 are amplified by preamp 352 and then pass through a first high pass filter 354. The high pass filtered signal is passed through an adjustable gain amplifier 356 which amplifies the signal by one of eight available multiplication factors under the control of digital signals on lines SEN:0, SEN:1 and SEN:2. The degree of amplification determines the effective lower or base sensing threshold, as discussed below.

The amplified signal is passed on through a first low pass filter 358, a second low pass filter 360, a second high pass filter 362 and an absolute value circuit 364 which produces at its output the absolute value of the previously filtered and amplified signal. In response to a blanking signal on line VHP2BLK, passage of signals through high pass filter 362 is prohibited for defined periods of time following delivery of atrial and ventricular pacing pulses, providing an additional blanking function. The duration of blanking in conjunction with a delivered atrial pacing pulse is preferably the same as blanking interval defined by the blanking signal on line VINB following delivery of an atrial pacing pulse. In conjunction with the delivery of a ventricular pacing pulse, the blanking period is substantially greater, for example, sixty or more milliseconds.

The output of the absolute value circuit 364 is provided to the detector circuit 366 which compares it to a defined sensing threshold to determine whether an R wave is to be detected or not. If the signal exceeds the threshold, detector circuit 366 provides an output on R-OUT line 202, which is provided to pacer timing and control circuit 212 (FIG. 2). The sensing threshold defined by detector circuit 366 is variable, and is adjusted in response to sensed ventricular events, delivered ventricular pacing pulses and is adjusted atrial pacing pulses. The detector 366 defines a basic or lower sensing threshold which is normally in effect, and a variable sensing threshold effective after sensed ventricular events and delivered atrial and ventricular pacing pulses. In order to be detected as an R wave, the signal from absolute value circuit 364 must exceed the greater of the lower or base sensing threshold and the variable threshold, as discussed in more detail below. Control of the effective sensing threshold following delivered atrial pacing pulses is controlled by signals on lines VBDET, VTCBLK and VREF. Adjustment of the effective sensing threshold following a delivered pacing pulse is accomplished by means of a reference voltage applied to the input of the detector 366 by the line VPRFR. Adjustment of the sensing threshold following a sensed R wave is a function of the amplitude of the sensed R wave as reflected by the output of absolute value circuit 364.

Figure 4:
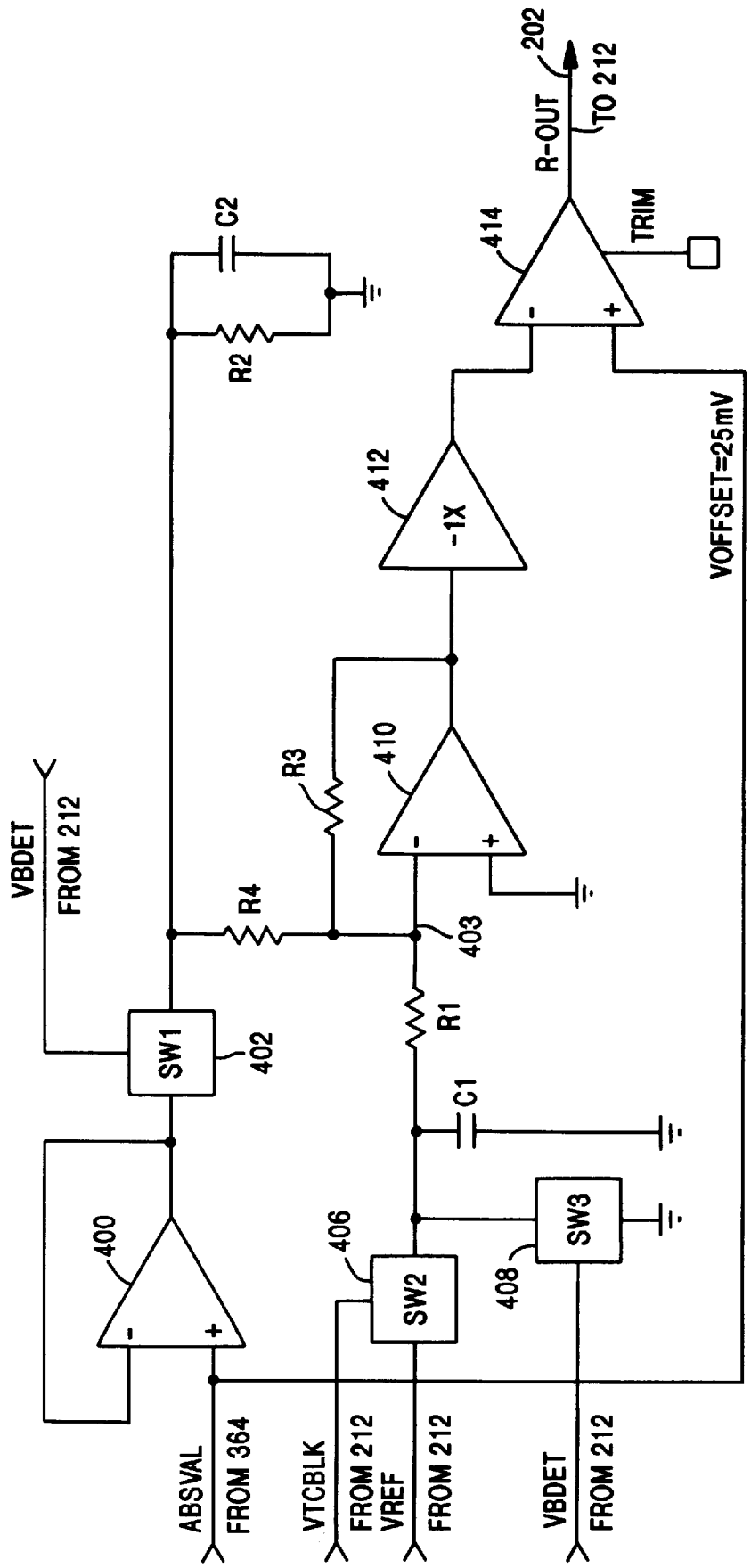
FIG. 4 is a functional schematic diagram illustrating the R-wave detection circuitry of the amplifier illustrated in FIG. 3

FIG. 4 illustrates detector 366 in more detail, and illustrates the manner in which the detector defines the various effective sensing threholds employed by the device. The amplified filtered R-wave signal from absolute value circuit 364 (FIG. 3) is applied to a comparator 414 which, in conjunction with the remainder of the illustrated circuitry defmes an adjustable sensing threshold. If the signal from the absolute value circuit exceeds the currently effective sensing threshold, a signal is generated on R-OUT line 202, which in turn is provided to the timing and control circuitry 212. The lower or base sensing threshold "S" is defined by the DC offset of the comparator circuit 414 in conjunction with the programmed amplification of the signal by amplifier 356. This sensing threshold is increased from the lower or base threshold following sensed R waves, delivered ventricular pacing pulses and delivered atrial pulses as follows.

A signal from absolute value circuit 364 corresponding to an R-wave passes through amplifier 400 which is configured to operate as an non-inverting peak voltage follower, and is applied via switch 1 (402) which is normally closed, to capacitor C2. This voltage reflects the amplitude of the sensed R-wave and is applied to comparator 414 via amplifier 410 and inverter 412, in conjunction with associated resistors R4 and R3 in such a fashion that the voltage stored on capacitor C2 is effectively increases the sensing threshold. The voltage on capacitor C2 decays over a relatively long time constant T1, determined by the values of R2 and C2 to provide a variable sensing threshold "$V_s(t)$". T1 may, for example, be an RC time constant of 450 milliseconds, providing for a gradual decay of the sensing threshold following a sensed ventricular depolarization in precisely the fashion described in conjunction with U.S. Pat. No. 5,117,824 issued to Keimel, incorporated by reference above. The variable sensing threshold $V_s(t)$ defines the effective sensing threshold until the variable sensing threshold $V_s(t)$ falls below the base or lower sensing threshold. The lower or base sensing threshold S is effective thereafter.

Following a delivered ventricular pacing pulse, on expiration of a blanking period defined by a blanking signal on line VHP2BLK (FIG. 3), a reference voltage is placed on line VPRFR (FIG. 3) and input into amplifier 400. In the same fashion as a sensed R-wave, this voltage signal also serves to recharge capacitor C2, providing an increased voltage threshold which decays from the value of the signal on line VPRFR, to define a variable sensing threshold $V_s(t)$ in the fashion described above following an R wave. The value of the reference signal on line VPRFR may be fixed or may vary as a function of the programmed base sensing threshold S.

Following a delivered atrial pacing pulse, the signal on line VBDET (FIG. 3) operates to open switch 402 and switch 408 which are normally closed. Opening switch 402 prevents adjustment of the variable sensing threshold $V_s(t)$ defined by capacitor C2 and resistor R2. This variable sensing threshold continues to decay, and is applied to the summing node 403 of amplifier 410 and then via inverter 412 to comparator 414. Concurrent with the opening of switches 402 and 408, switch 406 is closed in response to a signal on line VTCBLK, which passes a reference voltage on line VREF through to charge capacitor C1. The voltage on capacitor C1 is also applied to the summing node 403 of amplifier 410 and then via inverter 412 to comparator 414. The sum of the voltages on capacitors C1 an C2 thus serves to define the effective sensing threshold while the signal on line VREF is applied to capacitor C1. The signal on line VREF is applied to capacitor C1 for a preset interval, which may be, for example, 30 milliseconds, so that an increased sensing threshold is defined for this interval. The amplitude of the reference signal on line VREF may be fixed or may vary as a function of the value of the lower sensing threshold S.

When the signal on line VTCBLK terminates, the voltage on capacitor C1 is discharged via R1 to provide an exponentially decreasing sensing threshold $V_{ap}(t)$, in the same fashion as provided by resistor R2 and capacitor C2. However, the values of capacitors C1 and R1 are preferably chosen to define a much shorter time constant T2, which may be for example, 50 milliseconds. Allowing the sensing threshold to decay in this fashion assists in preventing incorrect detection of R waves as a result of an abrupt decrease in sensing threshold. After opening of switch 406, the signal on line VBDET terminates, closing switches 402 and 408. This in turn completes the discharge of capacitor C1, so that the effective sensing threshold is now once again the greater of the variable sensing threshold $V_s(t)$ and the base sensing threshold S.

The operation of the amplifier according to the present invention produces several benefits. By providing for an increased ventricular sensing threshold following a delivered atrial pacing pulse as opposed to simply blanking the ventricular amplifier, inappropriate sensing of the pacing pulse itself and of any post pacing polarization of the ventricular electrodes is prevented, while sensing of R-waves closely spaced to the delivered atrial pacing pulse is facilitated. By providing for an exponential decay of the increased threshold value following an atrial pacing pulse, inappropriate ventricular oversensing associated with an abrupt change in sensing threshold is avoided. These basic benefits of the present invention are disclosed in the context of an amplifier which also adjusts its sensing threshold following sensed R-waves and delivered ventricular pacing pulses. However, it is believed that the beneficial aspects discussed above may also be usefully employed in amplifiers which do not automatically adjust ventricular sensing thresholds following sensed R-waves or after delivered ventricular pacing pulses.

The description of the operation of ventricular amplifier 200 applies as well to the atrial amplifier 204, with the exception that the amplifier is coupled to electrodes 317 and 321 (FIG. 2) and that signals corresponding to those on lines VINB, VHP2BLK, VBDET, VTCBLK and VREF are instead generated at corresponding times following delivery of a ventricular pacing pulse, to provide an automatically adjusted effective sensing threshold. One additional difference between the implementation of the device in the context of the atrial sense amplifier 204 and the ventricular sense amplifier 200 may be that following a delivered atrial pacing pulse, the effective sensitivity is not adjusted, accomplished by simply omitting a signal corresponding to that on line VPRFR, described in conjunction with FIG. 3. In such case, the operation of the amplifier following a sensed atrial event does not correspond to that described in the above-cited Keimel et al patent.

Figure 5:
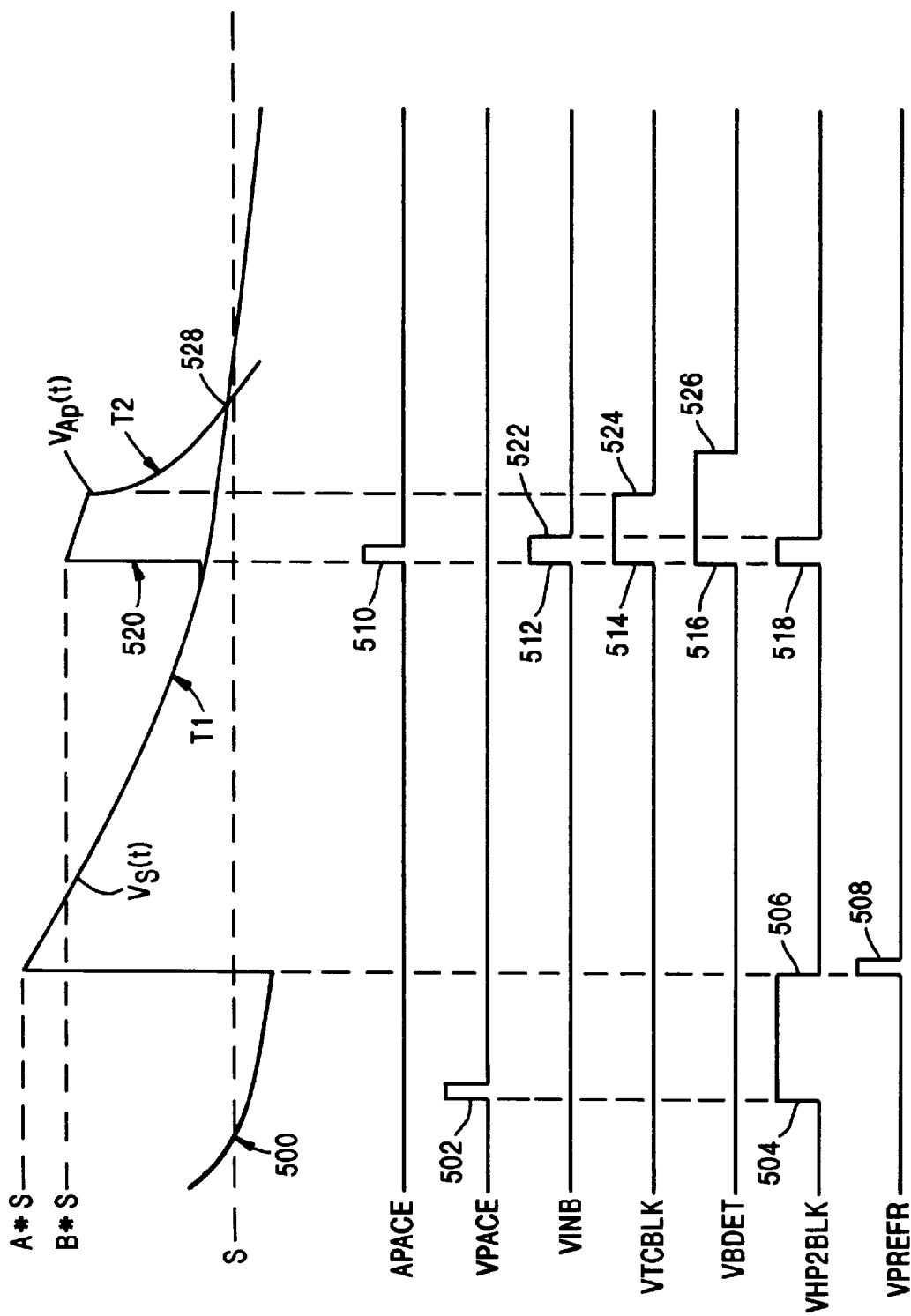
FIG. 5 is a timing diagram illustrating the operation of the circuitry illustrated in FIG. 4.

FIG. 5 is a timing diagram illustrating the operation of the detector 366 (FIG.3) to define the various variable sensing thresholds described above. The upper portion of FIG. 5 is a diagram illustrating the variable sensing thresholds $V_s(t)$ and $V_{ap}(t)$, discussed above. The variable sensing threshold $V_s(t)$ is, shown decaying below the base or lower sensing threshold S at 500. At 502, a ventricular pacing pulse is generated, which initiates a blanking signal on line VHP2BLK at 504. On expiration of the blanking signal on line VHP2BLK at 506, a reference voltage signal on line VPREFR is applied at 508 to the input of the detector 366 (FIG. 3) to increase the effective ventricular sensing threshold to a multiple A*S of the base sensing threshold. As discussed above, the value of A*S may be fixed or may vary as a function of the value of the base or lower sensing threshold S. The variable sensing threshold $V_s(t)$ decays thereafter according to time constant T1 as discussed above.

At 510, an atrial pacing pulse is delivered. Concurrent with delivery of atrial pacing pulse 510, a blanking signal on line VINB is initiated at 512, which disconnects the input of the amplifier from the ventricular electrodes via blanking circuit 350 (FIG. 3). Concurrent with initiation of this blanking signal, a threshold increase signal is generated on line VTCBLK at 514 which may persist, for example, for 30 milliseconds and which applies the voltage on line VREF to capacitor C1 (FIG. 4) to define an increased effective sensing threshold $V_{ap}(t)$ at 520. A signal on line VBDET is initiated at 516 which prevents modification of the variable sensing threshold $V_s(t)$ as discussed above. Also illustrated, a signal on line VHP2BLK provides for a blanking period corresponding to he duration of the signal on line VINB. During the time interval between the expiration of the input blanking signal on line VINB at 522 and the expiration of the threshold increase signal on line VTCBLK at 524, the amplifier operates to sense signals at an increased effective sensing threshold B*S, defined by the amplitude of the line of VREF (FIG. 4) added to the threshold defined by the voltage on capacitor C2. The value of this increase in sensing threshold, as discussed above, may be fixed, or may be varied as a function of the base or lower sensing threshold S. The value of B*S may be less than the value of increased threshold A*S. Following expiration of the increase threshold signal on line VTCBLK at 524, the effective sensing threshold $V_{ap}(t)$ (decays according to time constant T2 until expiration of the signal on line VBDET at 526, as discussed above. Consideration of the signal on line VBDET may be, for example, 60 milliseconds, to allow for substantial decay of the variable sensing threshold $V_{ap}(t)$, prior to discharge of capacitor C1 (FIG. 4).

While the above invention is described in the context of a dual chamber arrhythmia treatment device, in which it is believed to be particularly valuable, the present invention may also be applicable in other devices which sense in one chamber and pace in another chamber of the heart, including cardiac pacemakers which operate in pacing modes such as DDI mode, VVD mode, DDD mode, and the like. Alternatively, the invention may be usefully practiced in the context of pacemakers which pace both ventricles and/or both atria, for example as disclosed in U.S. Pat. No. 4,928,688, issued to Mower et al, U.S. Pat. No. 5,540,727, issued to Tockman et al., U.S. Pat. No. 5,403,356, issued to Hill et al. or U.S. Pat. No. 5,720,768 issued to Verboven-Nelisson, all of which are incorporated herein by reference in their entireties. In addition, while the invention is described above in the context of a device which employs sense amplifiers which provide for an automatically adjusted sensing threshold following sensed events and following pacing pulses delivered to the chamber to which the amplifier is coupled, the present invention may also be usefully employed in the context of devices which do not adjust the effective sensing thresholds following either or both of such events. Further, while the disclosed embodiment of the invention takes the form of a microprocessor controlled device, the invention is of course equally useful in the context of a device in which the various time intervals employed to control the sensing thresholds are determined by hardware, for example by a digital circuit employing dedicated logic, or by analog timers. The specific mechanism by which the time intervals associated with the operation of the adjustable threshold function are defined is not critical to successful use and enjoyment of the present invention. As such, the above disclosure should be taken as exemplary, rather than limiting, with regard to the claims which follow.

In conjunction with the above specification, I claim:

1. An implantable cardiac pacemaker having means for delivering pacing pulses to a first chamber of a patient's heart and means for sensing depolarizations of a second chamber of the patient's heart, wherein the means for sensing depolarizations of the second chamber of the patient's heart comprises:
   means for defining a base sensing threshold;
   means responsive to delivery of a pacing pulse to the first chamber of the patient's heart for defining a first increased sensing threshold greater than the base sensing threshold.

2. A pacemaker according to claim 1 wherein said means for defining said first increased sensing threshold comprises means for maintaining said first increased sensing threshold for a defined period of time following delivery of a pacing pulse to the first chamber of the patient's heart.

3. A pacemaker according to claim 1 or claim 2, wherein said means for defining said first increased sensing threshold further comprises means for defining a first variable sensing threshold gradually decreasing from said first increased sensing threshold to said base sensing threshold, following delivery of a pacing pulse to the first chamber of the patient's heart.

4. A pacemaker according to claim 3, wherein said sensing means further comprises means for defining a second increased sensing threshold following sensing of a depolarization in the second chamber of the patient's heart.

5. A pacemaker according to claim 4, wherein said means for defining said second increased sensing threshold further comprises means for defining a second variable sensing threshold decreasing from said second increased sensing threshold to said base sensing threshold, the second variable sensing threshold decreasing more slowly than said first variable sensing threshold.

6. A method of controlling an implantable cardiac pacemaker having means for delivering pacing pulses to a first chamber of a patient's heart and means for sensing depolarizations of a second chamber of the patient's heart, comprising:

defining a base sensing threshold;

responsive to delivery of a pacing pulse to the first chamber of the patient's heart, defining a first increased sensing threshold greater than the base sensing threshold.

7. A method according to claim 6 wherein defining said first increased sensing threshold comprises maintaining said first increased sensing threshold for a defined period of time following delivery of a pacing pulse to said first chamber of the patient's heart.

8. A method according to claim 6 or claim 7, further comprising defining a first variable sensing threshold gradually decreasing from said first increased sensing threshold to said base sensing threshold, following delivery of a pacing pulse to said first chamber of the patient's heart.

9. A method according to claim 8, further comprising defining a second increased sensing threshold following sensing of a depolarization in the second chamber of the patient's heart.

10. A method according to claim 9, further comprising defining a second variable sensing threshold decreasing from said second increased sensing threshold to said base sensing threshold, the second variable sensing threshold decreasing more slowly than the first variable sensing threshold.

* * * * *

UNITED STATES PATENT AND TRADEMARK OFFICE
CERTIFICATE OF CORRECTION

PATENT NO. : 6,058,327
DATED : May 2, 2000
INVENTOR(S) : Borgerding et al.

It is certified that error appears in the above-identified patent and that said Letters Patent is hereby corrected as shown below:

<u>Title page,</u>
Item [75], Inventors, third-named inventor "Gerald P. Borgerding" should read -- Gerald P. Arne --

Signed and Sealed this

Twenty-third Day of April, 2002

Attest:

Attesting Officer

JAMES E. ROGAN
*Director of the United States Patent and Trademark Office*